Dec. 23, 1975
D. J. S. BAILEY
ROSE PLANT
Filed May 10, 1973
Plant Pat. 3,819
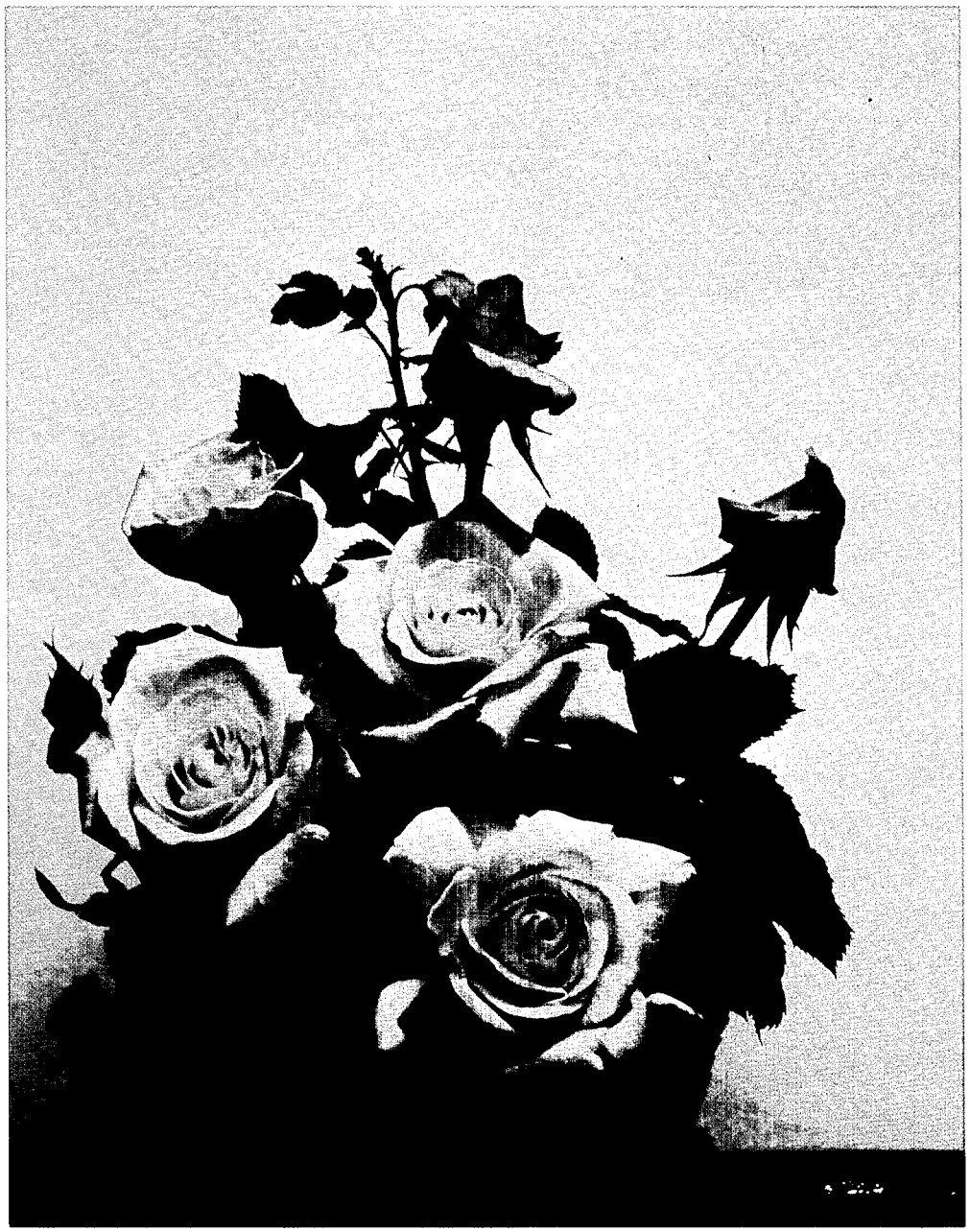

United States Patent

Plant Pat. 3,819

Patented Dec. 23, 1975

3,819

ROSE PLANT

Dorothy Jean Searles Bailey, Bakersfield, Calif., assignor to San Joaquin Rose Co., McFarland, Calif.

Filed May 10, 1973, Ser. No. 359,095

Int. Cl. A01h 5/00

U.S. Cl. Plt.—19 1 Claim

The present invention relates to a new and distinct variety of rose plant of the hybrid tea class. It was originated by me by crossing the rose variety known as John S. Armstrong as seed parent (Plant Pat. No. 2,056) with the variety known as Pink Peace as pollen parent (Plant Pat. No. 1,759).

As the result of this breeding, I have produced a new and improved rose variety which is distinguished from its parents, as well as from all other rose varieties of which I am aware, as evidenced by the following unique combination of characteristics which are outstanding therein:

(1) A neat, upright plant, developing new canes from the base of the plant in typical hybrid tea habit;
(2) Good adjustability to a wide range of soil and climatic conditions;
(3) Medium large, Dark Green foliage which is essentially disease resistant;
(4) Abundant bloom production from eary spring until late fall, with the flowers usually borne singly to a stem with long stems, or a loose cluster of two or three, each with a medium long stem, but in each case with strong stems and necks;
(5) Oval, pointed buds which open to high-centered blooms at the half open stage, said blooms being regular, well-imbricated, with 40–50 heavy, long-lasting petals;
(6) A distinctive and stable petal coloration in the bright pink range;
(7) A moderate tea fragrance.

In comparison with the parent varieties, this new variety has inherited many of its foliar characteristics from the paternal parent, Pink Peace. Both varieties have similar abundant, medium large foliage, usually in compounds of 5 leaflets, with dark green upper surface and light green lower surface to each leaflet. The stipules of the two varieties are indistinguishable, medium long, moderately narrow with medium points turning out at an angle of less than 45°, straight rather than recurved toward the stem. The mature thorns also are very similar. The bush habit resembles the maternal parent, John S. Armstrong, in the distinctive neat, upright habit. The petal coloration is intermediate between the two parents. Pink Peace is a medium pink, John S. Armstrong is a medium dark red, and this innovation is a rich hot pink.

This new variety somewhat resembles the variety known as Aquarius (Plant Pat. No. 3,128) in general plant habit and bloom size. However it is very easily distinguished by the difference in coloration. Aquarius has a blend of pink tones in all stages of the bloom; this variety is notable for the even distribution of the bright pink pigment on both the top and underside of each petal in all stages of the bloom.

The cross that resulted in this new variety was made in 1963 by me at Shafter, Calif. It was first asexually reproduced in 1965, also at Shafter, Calif., by means of budding. The distinguishing characteristics are held through succeeding propagations.

It was entered in the All American Rose Selections Trials, where it was known as 69R44. The fact that it received a top score for the 1969 AARS Trials is a matter of legal record.

The accompanying photographs show typical specimens of the vegetative growth and flowers of my new variety in different stages of development and are depicted in color as nearly true as it is reasonably possible with color photography.

The following is a detailed description of my new variety, with color terminology in accordance with the Horticultural Colour Chart of the British Colour Council and The Royal Horticultural Society Colour Chart (RHS) where such designation is used, except where general color terms of ordinary dictionary significance are obvious, as based upon observations of specimens grown at Shafter, Calif.:

TYPE: Half-hardy; medium-sized; upright bush habit; outdoor garden growing; seedling; for garden decoration and cut flowers.
CLASS: Hybrid tea.
BREEDING: Seedling.
Seed parent—John S. Armstrong.
Pollen parent—Pink Peace.
PROPAGATION: Holds its distinguishing characteristics through succeeding propagations by budding.

FLOWER

CONTINUITY: Continuous throughout the growing season.
FRAGRANCE: Moderate. Tea.
FLOWERS BORNE: Singly to a stem with long stems, or two or three to a stem, usually each on a medium long stem. Strong stems.
QUANTITY OF BLOOM: Free and abundant outdoors.
BUD:
Peduncle: medium in width and length, erect, medium green with red shading, entirely smooth.
Before calyx breaks: medium in size, oval pointed form; soft red glandular hairs; foliacious appendages on the surface; slender entire foliacious parts extending beyond the tip of the bud equal to ¾ or more of its length. Color: Pod Green o61, Plate 120, with Erythrite Red 0027/3, Plate 190.
As calyx breaks: No significant change.
As first petal opens: Size—Medium. Form—Urn shaped.
Opening: It opens well.
BLOOM:
Size when fully open—Medium, from 3 inches to 4½ inches.
Petalage—Very double; from 40 to 50 petals; arranged regularly; stamens seldom show.
Form—High-centered at first, generally holding throughout life of bloom; petals rolling outward slightly at first, loosely at maturity.
PETALS:
Texture—Thick. Appearance—Inside—Velvety. Outside—Satiny.
Shape—Outside—Round, apex circular. Intermediate—Ovate, apex slightly pointed. Inside—Ovate, apex smoothly circular or with one notch.

This description of a newly opened flower was made from a rose grown outdoors during the month of October at Shafter, Calif.:

Color—In the bud the color starts slightly redder than RHS 52a and gradually lightens.
Behavior—The petals of the spent bloom persist, gradually fading brown.
Flower longevity—On bush in garden—Five or more days in October. Cut roses grown outdoors and kept at living room temperature—4 days in October.

REPRODUCTIVE ORGANS

STAMENS: Medium number, arranged regularly about pistils, free from calyx.
Color—Bright yellow.
FILAMENTS: Medium length, most with anthers.
Color—Reddish.
ANTHERS: Medium size, open in sequence.
Color—Yellow.
POLLEN: Moderate quantity.
Color—Yellow.
PISTILS: Medium number.
STYLES: Uneven, medium long on outside, short on inside.
Color—White.
STIGMA: Color—Light yellow.
OVARIES: All enclosed in calyx.
HIPS: Medium small, oblong, smooth, walls moderately thick.
Color—Green yellow.
SEPALS: Permanent, moderately long; spear-shaped or retaining foliar characteristics.
Color—Brown.
SEEDS: One to ten large seeds, at least one usually protruding out the top of the ripe hip.

PLANT

FOLIAGE:
Leaves—Compound of five leaflets; abundant; medium large; moderately heavy.
Leaflets—Shape—Ovoid. Apex—Mucronate. Base—Round. Margin—Dentate-serrate.
Color—Mature—Upper surface—Dark green. Under surface—Light green. Young—Upper surface—Bronze with light green. Under surface—Bronze with light green.
Rachis (the supporting stem of the compound leaf)—Medium caliper. Upper side—Smooth. Under side—Slightly prickly.
Stipules—Medium long, moderately narrow with medium points turning out at an angle of less than 45°, straight rather than recurved toward the stem.

Disease resistance—Good average resistance to mildew, rust, and blackspot, as determined by comparison with other varieties grown under comparable cultural conditions at Shafter, Calif.
GROWTH:
Habit—Upright; well branched.
Growth—Vigorous.
Canes—Medium caliper.
Main stems—Color—Medium green. Thorns—Few, medium long, straight, pointing downward with narrow base; color—light brown. Prickles—None. Hairs—None.
Branches—Color—Medium bright green. Thorns—Few, medium small, straight, pointing downward with long narrow base; bronze. Prickles—Few; color—bronze. Hairs—None.
New shoots—Color—Bronze Red. Thorns—Several, short, straight, long narrow base; color—red. Prickles—Very few; color—red. Hairs—Very few, small; color—red.

I claim:

1. A new and distinct variety of rose plant of the hybrid tea class, substantially as herein shown and described, characterized particularly as to novelty by the unique combination of a neat upright plant of good vigor and typical hybrid tea habit of growth, good adjustability to a wide range of soil and climatic conditions, medium large, Dark Green foliage which is essentially disease resistant; abundant bloom production throughout the growing season, borne usually singly on long strong stems but also in loose clusters of two or three; oval, pointed buds which open to high-centered blooms that are distinctively regular and well-imbricated, with 40–50 long-lasting petals; a distinctive and stable petal coloration in the bright pink range, the general color effect of the opening bud being slightly redder than RHS 52a, the newly opened bloom RHS 52a, and the bloom three days open, slightly lighter than RHS 52a; and a moderate tea fragrance.

No references cited.

ROBERT E. BAGWILL, Primary Examiner